United States Patent [19]

Crespy

[11] Patent Number: 4,911,722

[45] Date of Patent: Mar. 27, 1990

[54] MECHANICAL SELF LOCKING FEMORAL PROSTHESIS AND A METHOD FOR IMPLEMENTING SAME

[75] Inventor: Gilles Crespy, 74 rue du Menhir, 29100 Douarnenez, France

[73] Assignees: Office Medico Chirurgical International S.A. (O.M.C.I.), Quimper; Gilles Crespy, Douarnenez; Marc Sailly, Quimper; Rene Kerberenes, La Foret Fouesnant, all of France; a part interest

[21] Appl. No.: 188,397

[22] PCT Filed: Aug. 6, 1987

[86] PCT No.: PCT/FR87/00309

§ 371 Date: Apr. 8, 1988

§ 102(e) Date: Apr. 8, 1988

[87] PCT Pub. No.: WO88/01492

PCT Pub. Date: Mar. 10, 1988

[30] Foreign Application Priority Data

Aug. 25, 1986 [FR] France .................. 86 12103

[51] Int. Cl.$^4$ .......................... A61F 2/36; A61F 2/30; A61F 5/04
[52] U.S. Cl. ........................................ 623/23; 623/18
[58] Field of Search ............ 623/23, 22, 18, 16, 623/21; 128/92 Y, 92 YL, 92 YT, 92 YK, 92 YW, 92 YY, 92 YZ

[56] References Cited

U.S. PATENT DOCUMENTS

| | | | |
|---|---|---|---|
| 2,381,050 | 8/1945 | Hardinge | 128/92 YT |
| 2,490,364 | 12/1949 | Livingston | 128/92 YK |
| 2,685,877 | 8/1954 | Dobelle | 128/92 YW |
| 3,846,846 | 11/1974 | Fischer | 623/23 |
| 4,530,115 | 7/1985 | Muller et al. | 623/18 X |
| 4,681,590 | 7/1987 | Tansey | 623/23 |
| 4,704,128 | 11/1987 | Frey | 623/16 X |
| 4,728,333 | 3/1988 | Masse et al. | 623/23 |

FOREIGN PATENT DOCUMENTS

| | | | |
|---|---|---|---|
| 0077868 | 5/1983 | European Pat. Off. | 623/22 |
| 0085147 | 10/1983 | European Pat. Off. | |
| 0170982 | 2/1986 | European Pat. Off. | 623/22 |
| 3528151 | 2/1987 | Fed. Rep. of Germany | 623/23 |
| 1049055 | 10/1983 | U.S.S.R. | 128/92 YY |

Primary Examiner—Richard J. Apley
Assistant Examiner—D. F. Crosby
Attorney, Agent, or Firm—Oblon, Spivak, McClelland, Maier & Neustadt

[57] ABSTRACT

The invention relates to a self locked mechanical femoral prosthesis and the method for implanting same. The shank (5) of the prosthesis (1) is separated into two parts (7) and (7'), and includes a slit (f) in which is introduced a rack (6). The profile of this latter cooperates with the internal profile of the mobile part (7) so that when the rack 6, under the action of a screw (8), undergoes a vertical movement, it causes a lateral movement of the mobile part (7) that widens the shank (5) of the prosthesis ensuring locking thereof in the bone.

5 Claims, 3 Drawing Sheets

MECHANICAL SELF LOCKING FEMORAL PROSTHESIS AND A METHOD FOR IMPLEMENTING SAME

FIELD OF THE INVENTION

The invention relates to a femoral prosthesis to be implanted in the upper end of the femur when the femoral head needs to be replaced because more particularly of traumatism or arthrosis. It also relates to the method of implementing same.

BACKGROUND OF THE INVENTION

In general, each femoral prosthesis includes a more or less long shank which is embedded in the femoral stump. The part which emerges therefrom is slanted with respect to the shank or stem by about 120° and serves as a base for a sphere which is intended to replace the femoral head.

Thousands of operations of this kind are carried out each year, which operation gives back a normal life to patients. For that, a greaty variety, as to shape and design, of prostheses exist, but these prostheses have certain drawbacks.

At the beginning, a standard shank was used which was locked in the femoral diaphysis with cement, but cement loses its mechanical properties in the long run, and almost all the feomral prostheses of this type finish by becoming loose with the years.

The ideal is then to do without cement and to lock the prosthesis right away by any means.

Some attempts have been made by implanting adjusted prostheses covered with microscopic roughnesses, force fitted, filling the femur to a maximum and which are rehabited by the bone in the months following the operation.

This technique has in fact two drawbacks, the first being the large number of prostheses in stock required so as to have the size which is exactly adapted to the femur of the patient, and the second being the risk of bursting the upper part of the femur due to the force fitting of these prostheses.

Compromises have been found such as the self locking prosthesis of the "Müller" type which is universally known.

Its shape is especially designed, but despite everything it uses a thin layer of cement.

OBJECT OF THE INVENTION

The object of the present invention is to overcome the above drawbacks and provides a prosthesis the shank of which includes a slit in which is fitted a mechanism capable, once the prosthesis is freely positioned in the medullar cavity, of moving away one of the pieces forming the shank, until the prosthesis is locked against the corticals.

SUMMARY OF THE INVENTION

The invention relates more precisely to a mechanical self locking femoral prosthesis including a Morse taper (3) and a shank (5) forming with the Morse taper (3) an angle corresponding to the cervico-diaphysial angle ($\alpha$), characterized in that it includes two parts (7) and (7') as well as a slit (f) of width (l) formed in the shank (5) over the whole of its length, in which slit is fitted a mechanism capable of providing controlled lateral movement of one of the parts (u) called mobile with respect to the other part (7') called fixed, as a function of the dimensions of the medullar cavity concerned.

BRIEF DESCRIPTION OF THE DRAWINGS

The invention will be better understood from the following explanations and the accompanying Figures in which.

For the sake of clarity, the same elements bear the same references in all the Figures.

DETAILED DESCRIPTION OF THE PRESENTLY PREFERRED EMBODIMENT

Figures 1, 2:
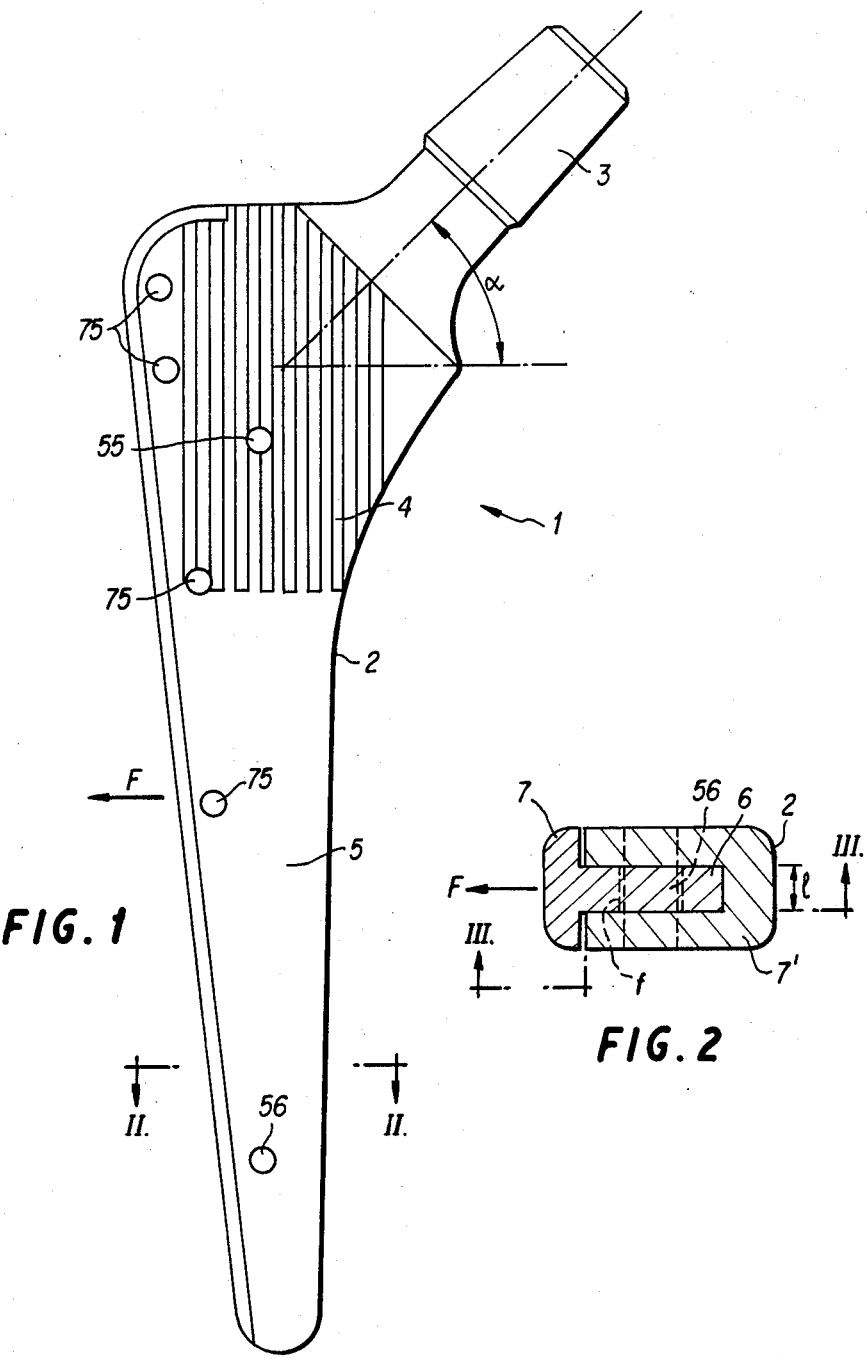
FIG. 1 is a view of the prosthesis in the initial state of introduction in the femoral stump.
FIG. 2 is a section of this prosthesis on the line II—II in FIG. 1.

A prosthesis 1, of the invention, shown in FIG. 1 in an external view, uses the same cervico-diaphysial angle, the same external profile 2, and the same Morse taper 3 receiving an adapted head as are to be found in a Müller's prosthesis. The lateral upper faces of the prosthesis have scores 4 so as to provide better holding of the prosthesis in the femoral stump, and the general surface condition is a porous or textured surface to aid fixation by bone ingrowth so as to allow rehabitation by the bone.

The resemblance with the prosthesis of the prior art stops there. In fact, one of the important characteristics of the invention resides in the fact that the part opposite the Morse taper 3 of the prosthesis (that is to say, the shank 5) has a vertical slit f of width l. In the slit f a cam rack 6 having a top 60 is fitted cooperating with the mobile part 7 of the shank 5 which is intended to move laterally along F under the action of the vertical thrust of the cam rack 6. Guide pins 55, 56 are provided.

Figure 3:
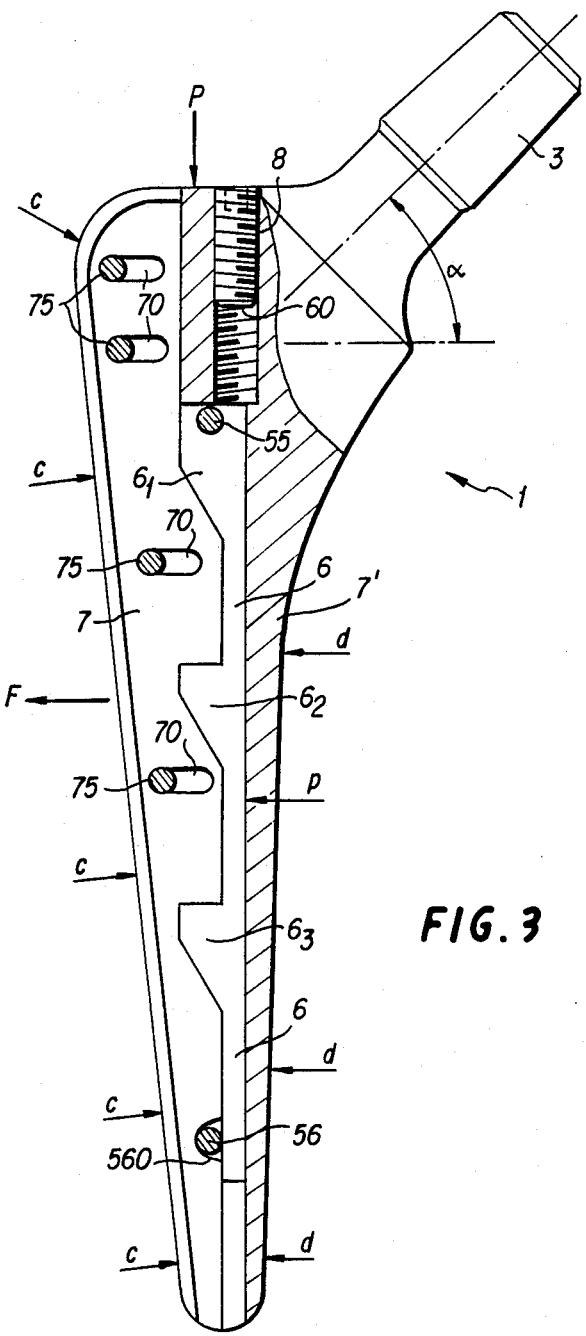
FIG. 3 is a broken section on the line III—III in FIG. 2, the prosthesis being in the initial state of introduction in the femural stump.
Figure 4:
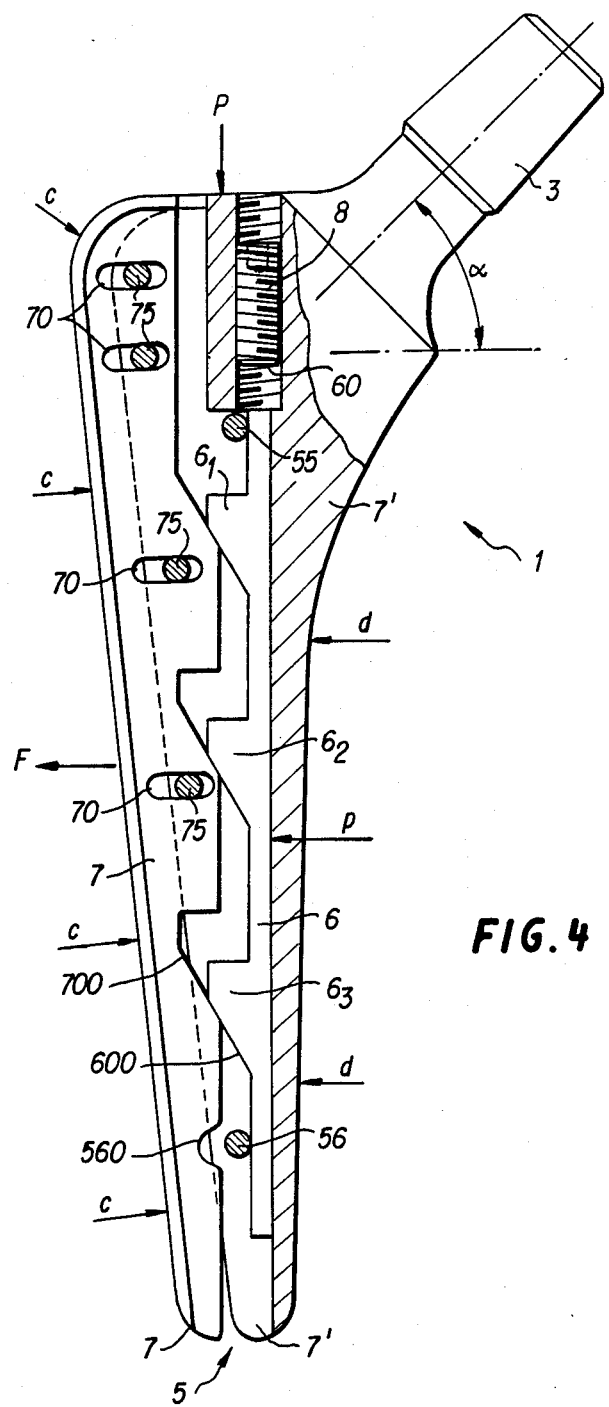
FIG. 4 is also a broken section on the line IV—IV in FIG. 21 in a configuration corresponding to a prosthesis widened by the internal mechanism of the invention.

This internal mechanism of the prosthesis of the invention is more clearly shown in FIGS. 3 and 4.

In FIG. 3, the internal mechanism is shown in the initial state, before the prosthesis 1 is fitted into the femural shank.

This mechanism is first of all formed by the cam rack 6 fitted into the vertical slit f of width l formed from top to bottom in the prosthesis body as far as the end of the shank 5, in the fixed part 7' thereof.

The cam rack 6 has a thickness equal to the width 1 of the vertical slit f. It will slide freely in the vertical slit f while bearing in the bottom of the vertical slit f on the plane p of the fixed part 7' of the shank 5.

On the side opposite the friction plane p of the cam rack 6, three cams $6_1$, $6_2$, $6_3$ are machined. The three cams $6_1$, $6_2$, $6_3$ have a right angled trapezoidal shape and are uniformly spaced apart over the whole height of the cam rack 6.

To maintain the cam rack 6 applied against the bottom p of the vertical slit f without hindering its free vertical sliding, the guide pins 55 and 56 situated at the top and the bottom of the prosthesis pass through the body and the shank 5 thereof from side to side.

A screw 8 placed vertically in the upper part of the body of the prosthesis 1 comes to bear by screwing on the top 60 of the cam rack 6. Since the cam rack 6 is imprisoned between the bottom p of the vertical slit f and pins 55 and the guide 56, it can only slide vertically.

The mechanism of the prosthesis 1 of the invention is also formed by the mobile part 7 the outer profile c of which is complementary to the profile d of the prosthesis 1.

The mobile part 7 is positioned in the vertical slit f so that it slides freely but only laterally. This sliding is obtained through the cam rack 6 and the cams $6_1, 6_2, 6_3$.

For that, the inner profile of the mobile part 7 is identical to that of the cam rack 6 on the same side as the cams $6_1, 6_2, 6_3$ so that these two profiles of the mobile part 7 and of the cam rack 6 fit one on the other. In the initial condition (FIG. 3), the mobile part 7 is in a retracted position in the prosthesis 1, the head of the screw 8 being flush with the upper plane P of the prosthesis.

So as to avoid any vertical movement of the mobile part 7, horizontal oblong holes 70 have been formed in the most appropriate zones of the mobile part 7 and cooperate with pins 75 which pass through the body of the prosthesis 1 from one side to the other. They serve as lateral guide for the mobile part 7, which may thus leave the vertical slit f laterally without undergoing a vertical movement. A recess 560 has been formed in the inner edge of the mobile part 7 so as to free the space occupied by the guide pin 56 guiding the cam rack 6.

Thus assembled, with its internal mechanism of the invention, the prosthesis 1 is ready for use. After preparation of the diaphysial cavity by the surgeon, the prosthesis is then driven in, free in this diphysial cavity. It only then remains to adjust the screw 8 for finally locking the prosthesis 1 of the invention in the femur.

This is what is shown in FIG. 4 where the screw 8 can be seen driven into its housing, over a certain length chosen arbitrarily and by way of example.

By screwing it in, the base of the screw 8 drives the top $60$ of the cam rack 6 which, moving vertically, pushes the mobile part 7 outwardly through the planes 600 and 700 of each cam $6_1, 6_2,$ and $6_3$ sliding on each other.

Since the pins 75 prevent any vertical movement of the mobile part 7, the mobile part 7 can only move aside laterally through the sliding of the horizontal oblong holes 70 on the pins 75.

Thus, by simply driving in the screw 8, the mobile part 7 is applied against the internal wall of the bone, providing mechanical locking of the prosthesis 1 in the bone without using cement.

The prosthesis of the invention may thus be widened to the desired dimensions by means of the internal mechanism when the prosthesis 1 is freely fitted into the femur so as to lock it perfectly against the corticals, according to any essential characteristic of the invention.

Since the stresses are thus distributed uniformly over the whole height of the femur, there is no fear of premature wear of the bearing zones. On the contrary, it is known that the corticals under stress thicken and become stronger giving a very reassuring radiological appearance. There is no risk of seeing the prosthesis badly fitted in varus with a conflict between the end of the shank of the prosthesis and the external cortical. Moreover, the possibility of breakage through fatigue either of the femur or of the shank of the prosthesis is eliminated because the clamping of the screw and the spreading out of the two parts of the shank necessarily places the prosthesis automatically back in the exact axis of the medullar cavity. It will be noted that the "prosthesis shoulder" (upper external corner) is more prominent than in conventional so called "Müller" prosthesis, so that it is literally encrusted in the spongy masses of trochanter.

With one or two types of prostheses in accordance with the invention in stock, almost all patients can be operated on. A prosthesis which corresponds, when closed, to a prosthesis of size 10 may, by use of the mechanism of the invention, once open take on the size of a prosthesis of size 15. Another which would be of size 15 when closed, could be adapted to particularly wide medullar cavities.

Since these prostheses are not fitted by force, there is no risk of bursting the femur. The prosthesis is fitted freely after preparation of the diaphysial cavity.

Numerous problems met with present day prostheses are thus solved, and in particular:

the absence of cement;

the avoidance of a stock of numerous costly prostheses of all sizes; and avoidance of the risk of bursting of the femur due to force fitting of the prosthesis.

Another important advantage of the femural prosthesis of the invention is that it allows the patient to walk immediately without a support, which is not always the case with present cementless prostheses.

In the prosthesis constructed in accordance with the invention, there is no particularly fragile part, no shaft receiving stresses, no spring in particular, and no moving parts. It is a question of metal masses sliding one on the other, machined very accurately so as to eliminate any play. Once in position, they will no longer move.

Moreover, in a preferred but not limitative variant, the prosthesis is made from titanium, which at the present time seems the material the best adapted to prosthetic implants of the hip.

Finally, although in a first stage this type of prosthesis is reserved for simply replacing the femural head in true cervical fractures of the femur, nothing opposes its use in coxarthrosis surgery with a prosthetic cotyle of a chosen model, within the field of complete plastic surgery of the cox a femoral articulation—that is to say, a total prosthesis of the hip.

I claim:

1. A mechanical self-locking femoral prosthesis comprising:
   (a) a first part having a longitudinally extending slit therein;
   (b) a second part slidably received in said longitudinally extending slit in said first part, the inner surface of said second part having at least one cam surface formed thereon;
   (c) first means for joining said first part to said second part so that they can move transversely with respect to each other but so that they cannot move longitudinally with respect to each other and so that they cannot pivot with respect to each other;
   (d) a cam rack:
      (i) received in said longitudinally extending slit between said first part and said second part;
      (ii) having a sliding surface that slides on said first part; and
      (iii) having at least one cam surface sized, shaped, and positioned to cooperate with said cam surface on said second part so that longitudinal movement of said cam rack causes transverse movement of said first and second parts with respect to each other; and (e) second means operable by a surgeon during implant of said prosthesis for moving said cam rack longitudinally relative to said first part.

2. A mechanical self-locking femoral prosthesis as recited in claim 1 wherein a Morse taper is mounted on said first part.

3. A mechanical self-locking femoral prosthesis as recited in claim 1 wherein:
   (a) said second means comprises a screw threadedly received in said first part in position to bear against said cam rack and
   (b) movement of said screw inwardly causes movement of said first and second parts away from each other.

4. A mechanical self-locking femoral prosthesis as recited in claim 1 wherein:
   (a) a plurality of cam surfaces are formed on said second part and
   (b) a corresponding plurality of cam surfaces are formed on said cam rack.

5. A mechanical self-locking femoral prosthesis as recited in claim 1 wherein said sliding surface of said cam rack is its inner surface.

* * * * *